Sept. 12, 1967 W. E. LAMMERTS Plant Pat. 2,766
ROSE PLANT
Filed May 9, 1966
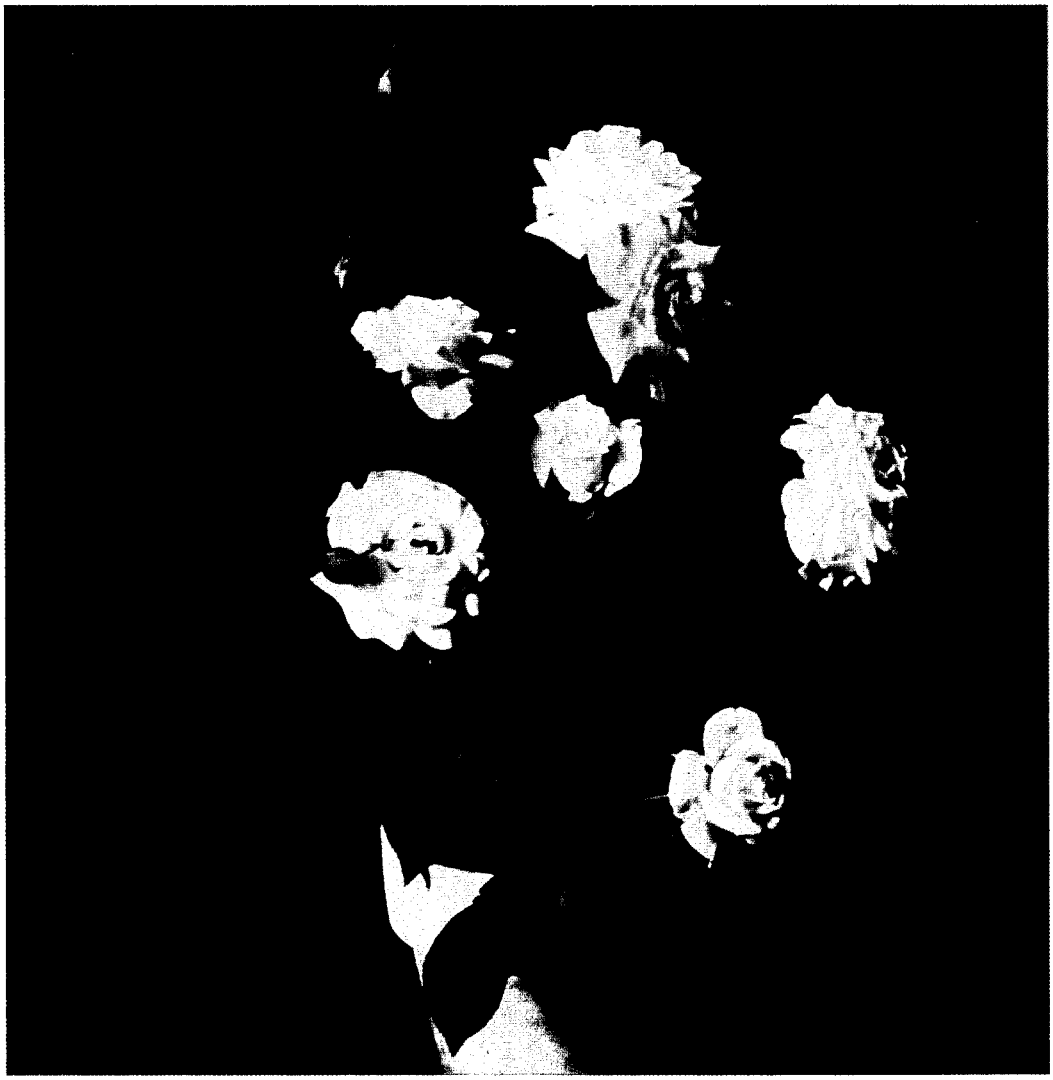

United States Patent Office

Plant Pat. 2,766
Patented Sept. 12, 1967

2,766
ROSE PLANT

Walter E. Lammerts, Watsonville, Calif., assignor to Amling-Devor Nurseries, Inc., Livermore, Calif., a corporation of California Filed May 9, 1966, Ser. No. 548,814
1 Claim. (Cl. Plt.—22)

The invention relates to a new and distinct variety of rose plant of the floribunda class originated by me in 1961 as a consequense of a breeding program begun in 1960. The parentage of my new rose plant is as follows: Rumba (Pl. Patent No. 1919), the seed parent, × Queen Elizabeth (Pl. Patent No. 1259), the pollen parent.

The object of the cross was to combine the larger flower size of Queen Elizabeth with the floribunda habit and flower substance of Rumba, thus getting a vigorous growing, high producing floribunda rose for greenhouse cut flower forcing. These objectives were achieved along with other desirable improvements, as evidenced by the following unique combination of characteristics which are outstanding in the new variety and which distinguish it from its parents as well as from all other varieties of which I am aware. My new variety is primarily characterized by: a marked improvement in petal substance when compared with Queen Elizabeth, a marked increase in flower size when compared with Rumba, an unusual deepening and enrichment of the coral-orange flower color with age and a high flower production, especially under greenhouse conditions.

Asexual reproduction of my new variety by budding through a series of annual propagations at Livermore, Calif., shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field grown, two year and greenhouse grown started eye plants at Livermore, Calif., from 1963 to date.

Plant upright, vigorous, robust, densely branched to about four feet. More or less continuously flowering throughout the growing season, with good winter blooming characteristics under glass. Profusely flowering, bearing as many as 200 flowers per year, outside and 40–50 under glass. The flowering stems are unusually long, developing from 6–9 expanded internodes. The flowers are borne in clusters of from 2–5 or singly. The mean and median number is 3 with a frequency of 3 flowered clusters of about 50%. The canes are green, becoming striately tan-gray with age. Thorns large, stout, with the point descending, about ½″ long x 5/16″ tall at base. The base is about ⅛″ wide. Thorns essentially of one size class, the smallest about ¼″, the largest ⅝″, 1–3 per internode. No prickles except on the peduncle, but numerous there. The thorns are tan-brown, reddish-based when young, very sharp, nearly opaque at an early age. The prickles are reddish-tipped, thin, 1/16″ long, translucent. The leaves are abundant, about 5–7 inches long, mostly 6 inches, with from five to seven leaflets, the lowermost pair being conspicuously smaller than the others. The leaves are dark green above, glossy, light green below, dull, with only the midvein being conspicuous. The leaves when young are Ox-Blood Red (00823) over Spinach Green (0960), appearing deep Garnet Brown (00918) above and 2–3 tones lighter below. The mature leaves are Spinach Green (0960) above and 0960/3 below. The leaf rachis is reddish above, grooved, green below and armed with a few hooked thornlets. New growth reddish, especially on the sunny side. Lateral branches are slightly zig-zag, especially distally. The terminal leaflets are about 2¾″ long x 1½″ wide, simply serrate, teeth variable. The lateral leaflets decrease in size proximally from about 2½″ x 1⅝″ to 1¼″ x ⅝ inches. The bracts are mostly simple, the lower most expanded, ligulately compound. The leaf subtending the inflorescence, usually 3 parted, otherwise normal, rarely reduced.

The sepals are ornate, about 1¾″ long x ⅜″ wide at base, the base connate, the tips are foliaceous, pinnately fimbriate, about ¼″ wide. The alternate sepals are ciliate, ½″ wide, hastate, only minutely ornate. The flowers are rich coral-salmon above, pink below. The limb of the petal is yellow above, white below. The petal is about 1½″ wide x 1¼″ long, mucronate and with a pronounced wavy margin. The eye is ½″ long. The peduncles are about 1¾ to 2″ long, quite constant in length and diameter, bristly. The bud is globular becoming urn shaped at anthesis. The bud at anthesis is about 1″ long. The color of the bud is orange. The fresh flower ¾″ open is rich coral-salmon, 2½–2½″ across, 1¼″ tall. The center is full, high, with the petals imbricated, spiraled. Fragrance is fruity, moderately intense. The fully open flower is about 2⅞–3″ across, with petaloids covering the gynoecium. The petal count is about 40–45; petaloids 10; stamenoids 10; stamens 75; ovaries 45. The hypanthium is about 7/16″ across x 5/16″ tall, urn shaped. The stigmas may be exserted 11/32″, but usually less (¼″). The petal color is venous and diffuse below. The yellow base color photolyses in 24–48 hours. The petal color when fresh is Poppy Red (16/1), edged Mandarin Red (16/2) above and Nasturtium Red (14/2) below. The petal color when old is Scarlet (19/2), to Geranium Lake (20/2), to Carmen (21/2), above, and Crimson (22/2) below.

Having thus disclosed my invention, I claim:

A new and distinct variety of rose plant of the floribunda class substantially as herein shown and described primarily characterized by: a marked improvement in petal substance when compared with Queen Elizabeth, a marked increase in flower size when compared with Rumba, an unusual deepening and enrichment of the coral-orange flower color with age and a high flower production, especially under greenhouse conditions.

No references cited.

ABRAHAM G. STONE, *Primary Examiner.*
ROBERT E. BAGWILL, *Examiner.*